US00PP11115P

United States Patent [19]

Enthoven

[11] Patent Number: Plant 11,115

[45] Date of Patent: Nov. 2, 1999

[54] GERANIUM PLANT NAMED 'MERITROPICAL'

[75] Inventor: Adrianus W. M. Enthoven, Wateringen, Netherlands

[73] Assignee: Enthoven Breeding B.V., Wateringen, Netherlands

[21] Appl. No.: 09/044,756

[22] Filed: Mar. 20, 1998

[51] Int. Cl.[6] ..... A01H 5/00

[52] U.S. Cl. ..... Plt./332

[58] Field of Search ..... Plt./332, 324

[56] References Cited

U.S. PATENT DOCUMENTS

P.P. 9,728 12/1996 Guillou et al. ..... Plt./332
P.P. 9,756 12/1996 Harring ..... Plt./332

*Primary Examiner*—Howard J. Locker
*Attorney, Agent, or Firm*—C. A. Whealy

[57] ABSTRACT

A new and distinct variety of Ivy Geranium plant named 'Meritropical', characterized by its rounded, initially upright, then pendant growth habit; moderate growth rate and vigor; fast rooting; medium green foliage color; numerous peduncles with 12 to 15 flowers per umbel; semi-double faint pink flowers; and good weather tolerance.

2 Drawing Sheets

BACKGROUND OF THE INVENTION

The present invention relates to a new and distinct variety of Ivy Geranium plant, botanically know as *Pelargonium peltatum*, and hereinafter referred to by the name 'Meritropical'.

The new Ivy Geranium is a product of a planned breeding program conducted by the inventor in Wateringen, The Netherlends. The objective of the breeding program was to develop compact Ivy Geranium varieties with semi-double flowers, fast rooting, good flower form, tolerance to Botrytis, weather resistance, compact and pendant growth habit, and attractive flower and foliage colors.

The new Ivy Geranium orginated from a cross made by the inventor of two proprietary seedling selections identified as code number A 134 as the female, or seed, parent and code A 246 as the male, or pollen, parent. The new Ivy Geranium was discovered and selected by the inventor as a flowering plant within the progeny of the stated cross in a controlled environment in Wateringen, The Netherlands, in June, 1992.

Compared to plants of the male parent, plants of the new Ivy Geranium are less compact and have larger flowers, Compared to plants of the female parent, plants of the new Ivy Geranium are more compact and have shorter peduncles. Additionally, flowers of plants of the female parent have more dark pink streaks than flowers of plants of the new Ivy Geranium.

Asexual reproduction of the new Ivy Geranium by terminal cuttings taken at Wateringen, The Netherlands, has shown that the unique features of this new Ivy Geranium are stable and reproduced true to type in successive generations of asexual reproduction.

SUMMARY OF THE INVENTION

The following traits have been repeatedly observed and are determined to be the unique characteristics of 'Meritropical'. These characteristics in combination distinguish 'Meritropical' as a new and distinct Ivy Geranium:

1. Rounded; initially upright, then pendant growth habit.
2. Moderate growth rate and vigor.
3. Fast rooting.
4. Medium green foliage color.
5. Numerous peduncles with 12 to 15 flowers per umbel.

6. Semi-double faint pink flowers.
7. Good weather tolerance.

The new Ivy Geranium can be compared to the Ivy Geranium variety 'Kleficharme' (not patented). Compared to plants of 'Kleficharme', plants of the new Ivy Geranium flower earlier, are more compact and have shorter and more numerous peduncles.

BRIEF DESCRIPTION OF THE PHOTOGRAPHS

The accompanying colored photographs illustrate the overall appearance of the new Ivy Geranium, showing the colors as true as it is reasonably possible to obtain in colored reproductions of this type.

The photograph on the first sheet comprises a top perspective view of a typical plant of 'Meritropical'.

The photograph at the top of the second sheet comprises a close-up view of a typical flower of 'Meritropical'.

The photographs at the bottom of the second sheet comprises a close-up view of typical leaves, upper surface is on the left and lower surface is on the right. Foliage and flower colors in the photograph may appear different from the actual colors due to light reflectance.

DETAILED BOTANICAL DESCRIPTION

The new Ivy Geranium has not been observed under all possible environmental conditions. The phenotype may vary somewhat with variations in environment such as temperature and light intensity, without, however, any variance in genotype. The following observations, measurements and comparisons describe plants grown in Wateringen, The Netherlands, under commerical practice in a glass-covered greenhouse with day temperatures of 20° C. and night temperature of 18° C. and light levels of 450 W/m$^2$.

In the following description, color references are made to The Royal Horticultural Sociey Colour Chart except where general terms of ordinary dictionary significance are used.

Classification:

*Botanical.*—*Pelargonium peltatum* 'Meritropical'.

*Commercial.*—Ivy Geranium.

Parentage:

*Male parent.*—Proprietary seedling selection code number A 246.

*Female parent.*—Proprietary seedling selection code number A 134.

Propagation:

*Type cutting.*—Terminal cuttings.

*Time to initiate and develop roots.*—Summer: About 16 days at 20° C. Winter: About 16 to 20 days at 20° C.

*Rooting habit.*—Vigorous, fast to root, freely branching.

Plant description:

*General appearance.*—Rounded; initially upright then pendant growth habit. Appropriate for 10.5 to 12 cm containers. About 12 weeks are required to produce a finished plant from an unrooted cutting.

*Growth rate.*—Moderate.

*Vigor.*—Moderate.

*Plant height.*—About 17 cm from soil surface to leaf plane; about 27 cm from soil surface to top of unbels.

*Branching habit.*—Moderate. Pinching (removal of terminal apices) is usually not required.

*Internode length.*—About 4.5 cm.

*Lateral branch length.*—About 25 cm.

*Foliage description.*—Arrangement: Alternate. Shape: Cordate, palmately lobed. Length: About 5.5 cm. Width: About 6.25 cm. Texture: Glabrous. Margin: Entire, lobed. Aspect: Upright and undulating towards the margin. Color: Young leaves, upper surface: 137A. Young leaves, lower surface: Darker than 144A. Fully expanded leaves, upper surface: 137A. Fully expanded leaves, lower surface: 144A. Venation pattern: Palmate. Petiole: Length: About 5 cm. Diameter: About 1.5 mm. Color: 146B. Durability to rain, wind and stress conditions: Very good.

Flowering description:

*Flowering habit.*—Flowers arranged in umbels.

*Natural flowering season.*—Spring throughout summer.

*Flower longevity.*—Flowers last about 2.5 weeks on the plant. Flowers self-cleaning.

*Flowers borne.*—Flower buds develop in apical leaf axils. Umbels are displaed above the foliage.

*Umbel.*—Form: Rounded. Quantity of flowers: Usually about 12 to 15 per umbel. Diameter: About 9 cm. Depth (height): About 4.75 cm.

*Flowers.*—Form: Semi-double. Diameter: About 4 cm. Depth (height): About 2.25 cm.

*Petals..*—Shape: Upper petals: Obtuse. Lower petals: Obovate. Apex: Rounded or slightly incised. Arrangement: Rosette, overlapping. Aspect: Mostly flat. Length: About 2.1 cm. Width: About 1.3 cm. Texture: Satiny, smooth. Margin: Entire. Color: Opened flower, upper petals, upper surface: 73D with dark pink stripes and dots, 67A/67B. Opened flower, upper petals, lower surface: 73D. Opened flower, lower petals, upper surface: 76D with dark pink stripes and dots, 67A/67B. Opened flower, lower petals, lower surface: 76D.

*Petaloids.*—Shape: Irregular, generally obovate with rounded or slightly incised apex. Quantity: Usually 2 to 5 per flower. Arrangement: Rosette, overlapping. Length: About 1.75 cm. Width: About 1.5 cm. Texture: Satiny, smooth. Margin: Entire. Color: Opened flower, upper petals, upper surface: 73D. Opened flower, upper petals, lower surface: 73D. Opened flower, lower petals, upper surface: 76D. Opened flower, lower petals, lower surface: 76D.

*Peduncle* (*umbel stem*).—Angle: Mostly erect, some horizontal. Length: About 17.5 cm. Diameter: About 4 mm. Texture: Pubescent. Color: Medium green.

*Pedicel* (*individual flower stem*).—Angle: Between 45 to 90° from vertical. Length: About 2.75 cm. Diameter: About 2 mm. Texture: Pubescent. Color: Medium to light green, reddish tones at proximal and distal ends.

*Flower bud.*—Shape: Elongated ovoid. Length: About 1 cm. Diameter: About 6 mm. Color: Medium to light green with reddish tones.

*Sepals.*—Shape: Narrowly lanceolate with acuminate apex and entire margin. Quantity: 5. Length: About 9 mm. Width: About 2 mm. Color: Light green with slight reddish tones.

*Reproductive organs.*—Androecium: Anther shape: Oblong. Anther size: About 2.5 mm. Anther color: Darker than 31A. Pollen color: Darker than 31A. Gynoecium: Pistil length: About 8 mm. Stigma shape: Decurrent. Stigma color: 61B. Style length: About 4 mm. Style color: 193B.

Disease resistance: No fungal, bacterial nor viral problems observed under commercial conditions.

Seed development: Seed production is very rarely observed.

It is claimed:

1. A new and distinct variety of Ivy Geranium plant named 'Meritropical', as illustrated and described.

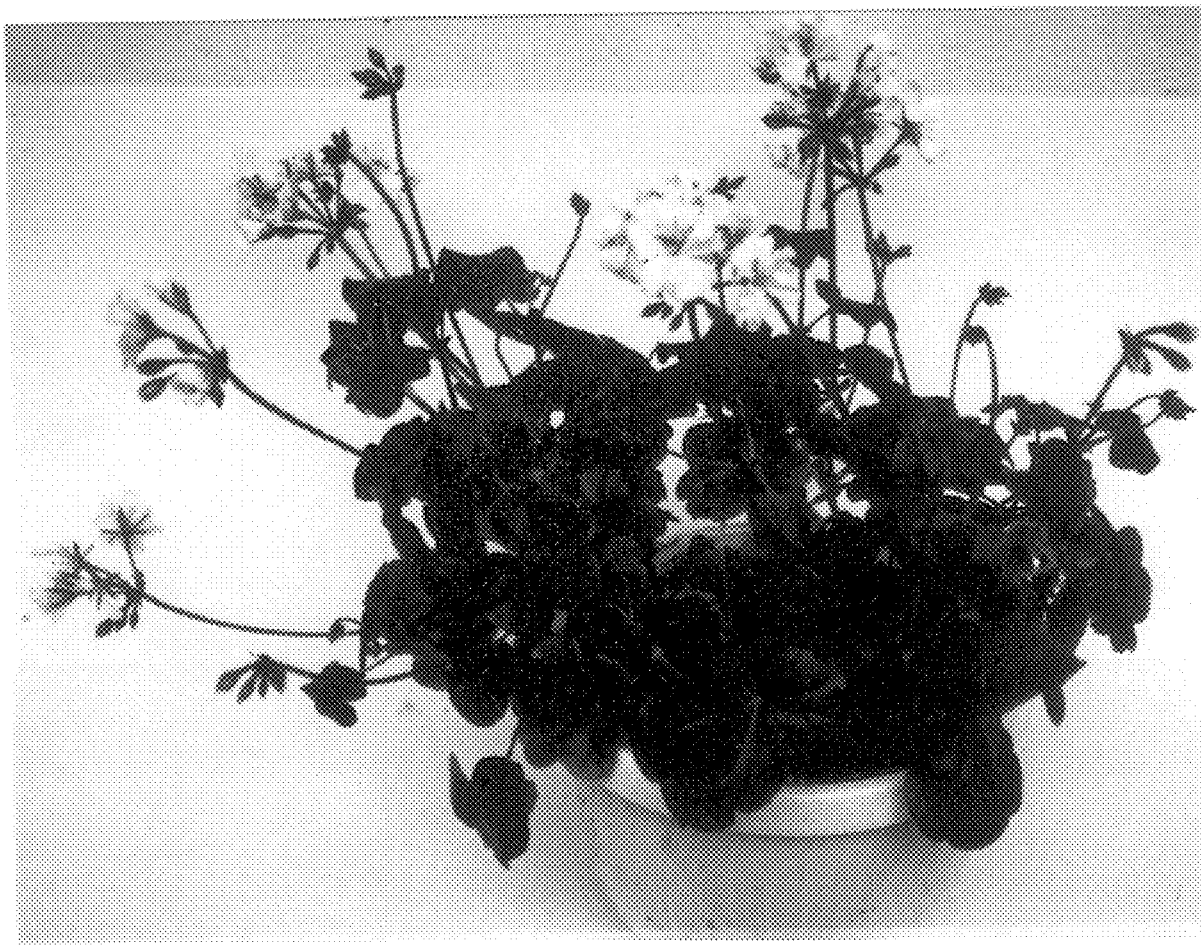

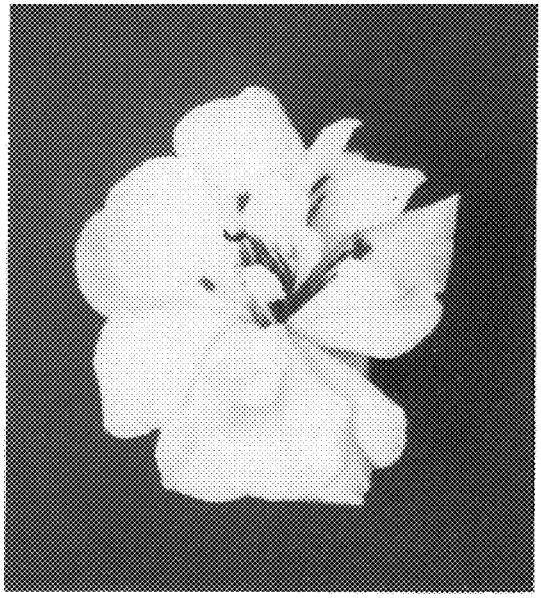
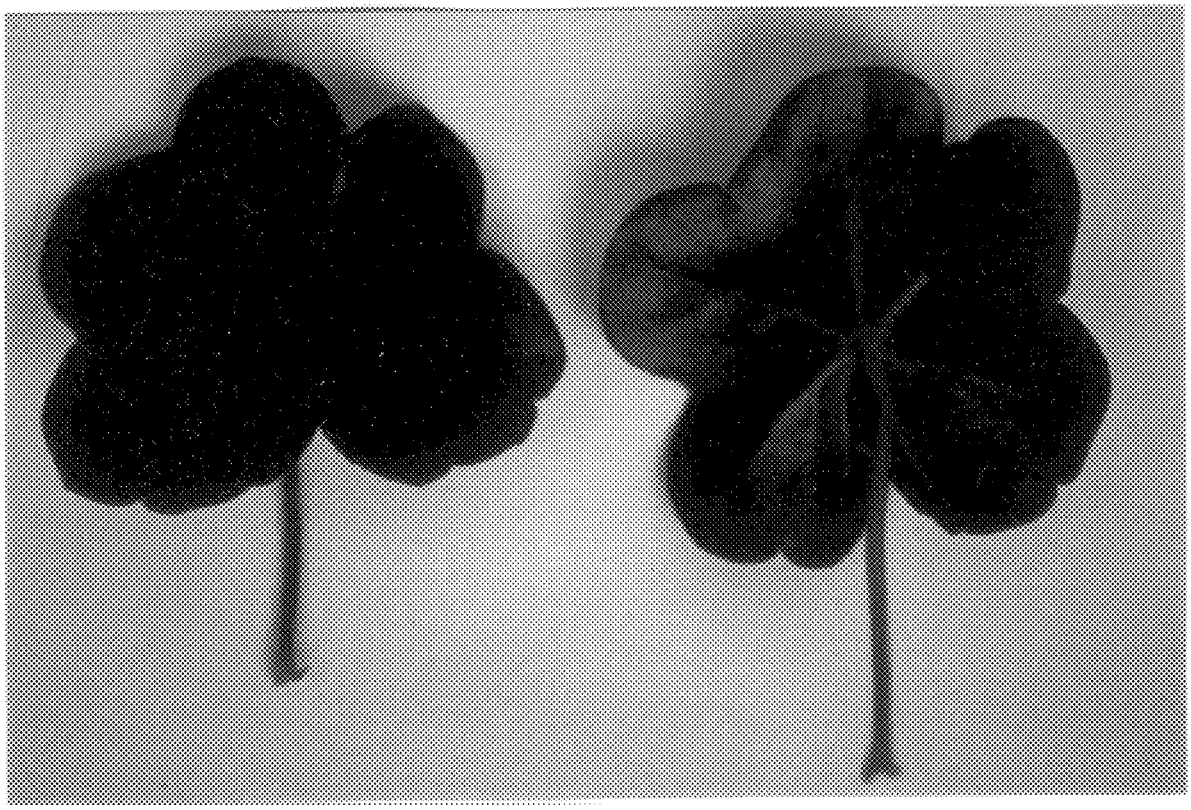

* * * * *